United States Patent
Heesch et al.

(10) Patent No.: US 10,702,668 B2
(45) Date of Patent: Jul. 7, 2020

(54) METHOD AND DEVICE FOR AUTOMATIC TUBE TRANSPOSITION DETECTION IN A VENTILATOR OR ANESTHESIA DEVICE

(71) Applicant: Drägerwerk AG & Co. KGaA, Lübeck (DE)

(72) Inventors: Ralf Heesch, Lübeck (DE); Robert Schmid, Lübeck (DE); Jonas Börner, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 1085 days.

(21) Appl. No.: 15/159,198

(22) Filed: May 19, 2016

(65) Prior Publication Data

US 2016/0346497 A1 Dec. 1, 2016

(30) Foreign Application Priority Data

May 29, 2015 (DE) .................... 10 2015 006 719

(51) Int. Cl.
*A61M 16/08* (2006.01)
*A61M 16/01* (2006.01)
(Continued)

(52) U.S. Cl.
CPC .... *A61M 16/0833* (2014.02); *A61M 16/0051* (2013.01); *A61M 16/0072* (2013.01);
(Continued)

(58) Field of Classification Search
CPC .............. A61M 16/00; A61M 16/0051; A61M 16/0072; A61M 16/01; A61M 16/021;
(Continued)

(56) References Cited

U.S. PATENT DOCUMENTS

| | | | |
|---|---|---|---|
| 4,413,632 A | 11/1983 | Schlessinger et al. | |
| 5,439,355 A * | 8/1995 | Jimison | A61M 5/16854 417/63 |

(Continued)

FOREIGN PATENT DOCUMENTS

| | | |
|---|---|---|
| DE | 41 11 965 A1 | 10/1992 |
| WO | 2014/068000 A1 | 5/2014 |

*Primary Examiner* — Justine R Yu
*Assistant Examiner* — Matthew R Moon
(74) *Attorney, Agent, or Firm* — McGlew and Tuttle, P.C.

(57) ABSTRACT

A ventilator or anesthesia device and method create a reference state and record a measured value as a reference value. A gas delivery unit is activated after the ending of the reference state to build up pressure in a breathing circuit. A comparison measured value is determined with a pressure or flow sensor. A deviation of the measured value from the reference value in relation to a predefined or predefinable expected value is monitored based on the comparison. A warning message is issued depending on a result of the comparison. A drop in pressure in the breathing circuit is caused after the recording of the comparison measured value and a further comparison measured value is recorded following the drop in pressure. A deviation of the further comparison measured value from the reference value leads to a further warning message when the deviation does not correspond to the further expected value.

17 Claims, 5 Drawing Sheets

(51) Int. Cl.
*A61M 16/00* (2006.01)
*A61M 16/20* (2006.01)
*A61M 16/22* (2006.01)
*A61M 16/10* (2006.01)

(52) U.S. Cl.
CPC .......... *A61M 16/01* (2013.01); *A61M 16/021* (2017.08); *A61M 16/085* (2014.02); *A61M 16/0875* (2013.01); *A61M 16/101* (2014.02); *A61M 16/208* (2013.01); *A61M 16/22* (2013.01); *A61M 2016/003* (2013.01); *A61M 2016/0027* (2013.01); *A61M 2016/1025* (2013.01); *A61M 2205/14* (2013.01); *A61M 2205/3331* (2013.01); *A61M 2205/50* (2013.01); *A61M 2230/435* (2013.01)

(58) Field of Classification Search
CPC .. A61M 16/101; A61M 16/208; A61M 16/22; A61M 2016/1025; A61M 2205/50; A61M 2230/435; A61M 2039/1005; A61M 2039/1044; A61M 2039/1094; A61M 16/0003; A61M 16/0045; A61M 16/022; A61M 16/08; A61M 16/0816; A61M 16/0841; A61M 16/0858; F17D 5/02; F17D 5/06; G01M 3/00; G01M 3/04; G01M 3/20; G01M 3/26–34
USPC .................................. 137/15.11; 73/40–49.3
See application file for complete search history.

(56) References Cited

U.S. PATENT DOCUMENTS

| | | | |
|---|---|---|---|
| 5,873,361 A | | 2/1999 | Hakala |
| 6,139,519 A | * | 10/2000 | Blythe ................ A61M 13/003 600/560 |
| 6,237,592 B1 | | 5/2001 | Surjadi et al. |
| 6,571,796 B2 | * | 6/2003 | Banner ................ A61M 16/20 128/204.16 |
| 8,230,858 B2 | | 7/2012 | Karlsson |
| 2003/0214412 A1 | * | 11/2003 | Ho .................... A61M 5/14228 340/611 |
| 2008/0053441 A1 | * | 3/2008 | Gottlib .............. A61M 16/0051 128/204.23 |
| 2008/0202526 A1 | | 8/2008 | Heinonen |
| 2010/0078018 A1 | | 4/2010 | Heinonen et al. |
| 2015/0273172 A1 | * | 10/2015 | Pessala ............ A61M 16/0051 128/203.12 |

* cited by examiner

METHOD AND DEVICE FOR AUTOMATIC TUBE TRANSPOSITION DETECTION IN A VENTILATOR OR ANESTHESIA DEVICE

CROSS REFERENCE TO RELATED APPLICATIONS

This application claims the benefit of priority under 35 U.S.C. § 119 of German Patent Application 10 2015 006 719.2 filed May 29, 2015, the entire contents of which are incorporated herein by reference.

FIELD OF THE INVENTION

The present invention pertains to a method for the automatic detection of a fluidic connection state of a ventilator (also known as a respirator) or anesthesia device, particularly for the automatic detection of incorrectly connected, transposed ventilation tubes. The present invention pertains, furthermore, to a ventilator or anesthesia device, sometimes designated below in summary as medical device or briefly only as device, as a device for carrying out the method. Transposition of the ventilation tubes is defined as a state, in which the, in principle, intended connection, on the one hand, of an inspiratory fluidic port and, on the other hand, of an expiratory fluidic port of a medical device with a connection of a so-called Y-piece in each case is not established by means of two ventilation tubes, but rather the two ports of the device are connected by means of one ventilation tube and the two connections of the Y-piece are connected by means of the other ventilation tube.

BACKGROUND OF THE INVENTION

In case of a necessary ventilation of a patient by means of a medical device intended for this, it is, as is known, to be ensured that the ventilation tubes of the device are connected correctly and are not transposed and thus a safe ventilation of the particular patient can be carried out. The corresponding checking is carried out by the user of the device, i.e., usually medical staff. The checking comprises individual checking steps to be carried out manually and is usually carried out in conjunction with the switching on of the device or a brief leak test.

However, a sometimes quite large number of tubes and cables in the patient area may result in ventilation tubes being connected incorrectly in practice.

SUMMARY OF THE INVENTION

An object of the present invention is to provide a method and a device implementing the method, in which method or in which device a possible transposition of the ventilation tubes is detected with certainty by means of an automatic tube transposition detection and an automatic indication to the user can occur based on such a detection.

This object is accomplished according to the present invention by means of a method for the automatic detection of transposed ventilation tubes, i.e., for the automatic detection of a corresponding special fluidic connection state of a ventilator or an anesthesia device. Provisions are made with regard to the device for the device to comprise at least one gas delivery unit, a measuring device, at least one sensor and a control unit, an inspiratory fluidic port, an expiratory fluidic port and, further, a fluid measuring port, which is coupled with the at least one sensor. A part of a breathing circuit, which can be completed with at least one ventilation tube, is formed in the interior of the device up to the inspiratory and expiratory fluidic ports, each acting as an interface. The inspiratory fluidic port and the expiratory fluidic port can be coupled to a Y-piece by means of ventilation tubes and are coupled to the Y-piece in case of a correct connection. The fluid measuring port can be coupled to the Y-piece by means of a sample gas line and is coupled to the Y-piece in case of a correct connection. In principle, the sensor may be located, for example, also at the Y-piece itself and thus in the direction of flow in front of the sample gas line. The sample gas line is provided for feeding a gas sample, which can be derived at the Y-piece, from the breathing circuit to a measuring device.

The part of the breathing circuit that can be completed with at least one ventilation tube in the interior of the device comprises a so-called inspiratory branch as well as a so-called expiratory branch. The two branches are led to a port of the device each, i.e., an inspiratory port as well as an expiratory port. The ventilation tubes can be connected to these ports. In case of the transposition of the ventilation tubes outlined in the introduction, the two ports are connected to one another by means of one ventilation tube (short-circuit). The part of the breathing circuit located in the interior of the device is also completed to form a closed breathing circuit by means of such an incorrect connection of the two ports. In case of a correct connection of the ventilation tubes, a ventilation tube originating from the inspiratory port and a ventilation tube originating from the expiratory port are connected by means of a so-called Y-piece. The part of the breathing circuit located in the interior of the device is completed to form a closed breathing circuit in case of such a correct attachment of the ventilation tubes as well. A further ventilation tube leads to the ventilated patient downstream of the Y-piece.

A state expected in the breathing circuit, for example, a pressure corresponding or at least essentially corresponding to a predefined or predefinable expected value, results because of the operation of the gas delivery unit during a predefined operating state. For this, the Y-piece is closed during the test, i.e., during the course of the method, for example, by the Y-piece being deposited in a so-called parking holder and by this bringing about the closing of the Y-piece.

The determination of a comparison measured value chronologically correlated with a predefined operating state of the gas delivery unit, i.e., for example, a state, in which pressure is built up in the breathing circuit, especially in the inspiratory branch, by means of the gas delivery unit, or a state, in which a predefined gas concentration is built up in the breathing circuit by means of the gas delivery unit, guarantees a comparability of the determined comparison measured value with a particular expected value. The control unit controls both the gas delivery unit and the determination of the comparison measured value such that the determination of the comparison measured value chronologically correlated with the particular operating state of the gas delivery unit is easily possible. The comparison of the determined comparison measured value with the expected value is also carried out by means of the control unit. The possible issuing of a warning message, i.e., for example, the activation of an optical and/or acoustic signal or display element, depending on the result of the comparison, is likewise carried out by means of the control unit.

Just as by means of the method explained above, the above-mentioned object is accomplished by a device in the form of a medical device of the type mentioned in the introduction having the features according to the invention.

Provisions are made for this in the medical device for this medical device to consequently comprise, for carrying out the method outlined above and described with further details below, a gas delivery unit, a measuring device, at least one sensor and a control unit, an inspiratory fluidic port, an expiratory fluidic port and, further, a fluid measuring port, which is coupled with the at least one sensor, wherein the inspiratory fluidic port and the expiratory fluidic port can be coupled to a Y-piece by means of ventilation tubes. The medical device and especially the control unit thereof are intended for this and configured to carry out the method.

A central advantage of the approach according to the invention is that a possible transposition of the ventilation tubes can be automatically detected and is automatically detected within the framework of carrying out the method or of the operation of the medical device. In the case of transposed ventilation tubes, when the inspiratory fluidic port and the expiratory fluidic port of the device are short-circuited by means of a ventilation tube, none of the ventilation tubes is connected to the Y-piece. The conditions arising because of the predefined operating state of the gas delivery unit in the breathing circuit thus neither concern the Y-piece nor the sample gas line coupled to the Y-piece in case of a correct connection at least in this respect. A comparison measured value recorded by means of the sensor and the measuring device in relation to the sample gas line will therefore not correspond to a value, as it would result in case of a correct connection of the ventilation tubes to the Y-piece (expected value). The result of the comparison makes the transposition of the ventilation tubes automatically detectable, i.e., by means of the control unit, and a warning message can correspondingly be issued on this basis. When the sensor is not coupled to the Y-piece, because the sample gas line is not connected to the Y-piece, or not correctly, the state of an incorrect connection is present. Even in case of ventilation tubes correctly connected to the Y-piece, the conditions arising because of the predefined operating state of the gas delivery unit in the breathing circuit have no effect on the comparison measured value that can be determined by means of the sensor. In this case as well, the comparison of the comparison measured value with an expected value makes the incorrect connection automatically detectable and a warning message can correspondingly also be issued on this basis.

As a result, the detection of a fluidic connection state in the form of an incorrect connection or of a possible transposition of the ventilation tubes is no longer dependent on whether the staff carries out a manual test in relation to the correct attachment of the ventilation tubes before the beginning of ventilation. The use of the medical device is more reliable and the medical staff is not burdened with manual, time-consuming and error-prone tests.

In the case of an anesthesia device of the applicant, known under the trademark ZEUS, the Y-piece is plugged onto a port with a valve. It is thereby possible to build up pressure at the ventilation tubes by means of the gas delivery unit and subsequently to ensure a release of pressure via the valve. When a drop in pressure is detected at a pressure sensor at the inspiratory port or at the expiratory port, the ventilation tubes are correctly connected to the Y-piece. By contrast to the test method suggested here and below, a method using an additional valve at the Y-piece or at the parking holder is more costly because only functional units, which a medical device with ventilation tubes, especially an anesthesia device, has anyway, are used in the test method according to the invention instead of an additional valve.

A method, in which a differential pressure value is recorded by means of a sensor at an anesthesia device and a pump of a sample gas line is switched on or switched off every time the differential pressure value exceeds or falls below a threshold value, is known from U.S. Pat. No. 8,230,858 B2. It shall be thereby achieved that the pump of the sample gas line is only active if a ventilation at the patient is actually intended such that the activation of the pump only as needed results in less wear of the pump.

A ventilator is well known from WO 2014/068000 A1, in which a leak state of ventilation tubes is checked by a pressure signal being sent into the ventilation tubes by means of a gas delivery unit and a pressure value then being measured by means of a sensor of a gas sample line, which is compared to a reference value in order to determine whether a leak state is present.

An anesthesia ventilator is known from US 2008/0202526 A1, in which a leak state is detected by a gas with a predetermined gas concentration being introduced into ventilation tubes, and then the introduction of the gas of the predetermined gas concentration is monitored via a sensor unit at a gas sample line.

A method for the detection of a leak state in an anesthesia device, in which flow sensors are used, is known from US 2010/0078018 A1.

A method for the automatic calibration of a pressure sensor is known from U.S. Pat. No. 6,237,592 B1.

A method for the calibration of a flow sensor of a breathing system is known from DE 41 11 965 A1, in which an opening and closing of the ventilation circuit is provided for calibrating or detecting a reference value for a flow measurement.

A method for the operation of a ventilator, in which the ventilator circuit can be ventilated for the calibration, is known from U.S. Pat. No. 5,873,361 A.

A reference state is additionally created before determining the comparison measured value. During the reference state, i.e., for example, after passing a predefined or predefinable period of time after the initiation of the reference state, a measured value is recorded and temporarily stored as a reference value for purposes of standardization. The reference state is ended after the recording of the reference value. The reference state is automatically created and ended by means of the control unit by this control unit activating at least one functional unit comprised by the device for this in a corresponding manner. After the ending of the reference state, the gas delivery unit is activated for creating the predefined operation state thereof. After the activation of the gas delivery unit, for example, after passing a predefined or predefinable period of time, the comparison measured value (a built up pressure comparison measured value) already mentioned in conjunction with the general form of the method is determined by means of the sensor and the measuring device. A deviation of the (built up pressure) comparison measured value from the reference value in relation to the predefined or predefinable expected value is monitored by means of the likewise already mentioned comparison.

This has the advantage that a standardization of the comparison measured value recorded later is possible by means of the additional consideration of a reference value. The standardization occurs by a deviation of the comparison measured value from the reference value in relation to the expected value being taken into consideration. In the simplest case, such a deviation is a difference between the comparison measured value and the reference value, as a result of which the above-mentioned standardization is obtained. The standardization defines, as it were, a zero point or reference point and, in relation thereto, increasing or decreasing measured values as well as rising or falling flanks in a measured value curve can be especially easily automatically detected. The predefining of an expected value suitable for use within the framework of the method becomes easier by taking this deviation into consideration in relation to the expected value. Besides the expected value, a certain tolerance range above and below the expected value is usually taken into consideration as well. In case of the standardization of the comparison measured value obtained with the embodiment of the method, the tolerance range may be selected to be smaller than this would be possible without such a standardization. The automatic analysis of the comparison measured value is thus more reliable.

In a special embodiment of the method providing a standardization of the comparison measured value, the device comprises, in addition to the gas delivery unit and the control unit, at least one venting device as well as the already mentioned sensor in the form of a pressure sensor. The reference state is created by the breathing circuit being vented (being opened) by opening with the venting device. After the venting (opening) of the breathing circuit, a pressure measured value is recorded as a reference value by means of the pressure sensor for purposes of standardization. The reference state is ended after the recording of the reference value by the venting of the breathing circuit being ended by closing the breathing circuit with the venting device. The opening and closing of the venting device occurs automatically in each case under the control of the control unit and because of a corresponding activation by the control unit. After the ending of the reference state, the predefined operating state of the gas delivery unit is automatically created. For this, the gas delivery unit is activated by means of the control unit for the buildup of pressure in the breathing circuit and a pressure is built up in the breathing circuit by means of the activated gas delivery unit. After the activation of the gas delivery unit, for example, after passing a predefined or predefinable period of time, a pressure measured value is automatically recorded by means of the pressure sensor and the measuring device in relation to the resulting buildup of pressure as a comparison measured value because of a corresponding activation by the control unit. Finally, after the recording of the comparison measured value, a deviation of the comparison measured value from the reference value in relation to the predefined or predefinable expected value is checked by means of the control unit within the framework of the comparison. At the end of the method, a warning message is issued by means of the control unit or at least under the control of the control unit when the deviation does not or does not at least essentially correspond to the expected value.

In an additional special embodiment of the method providing a standardization of the measured value, the device comprises, in addition to the gas delivery unit and the control unit, at least one venting device as well as the sensor in the form of a gas concentration sensor. In this embodiment of the method, the reference state is created by the breathing circuit being flushed with a first test gas having a predefined or predefinable composition. After that, a gas concentration value is recorded as a reference value by means of the gas concentration sensor for purposes of standardization. Again, the reference state is ended after that. The creation and the ending of the reference state as well as the recording of the reference value occur corresponding to the above explanations by means of the control unit and under the control thereof. After the ending of the reference state, the gas delivery unit is activated by means of the control unit and the breathing circuit is flooded with a second test gas having a likewise predefined or predefinable composition. After the activation of the gas delivery unit, a further gas concentration value is recorded as a comparison measured value by means of the gas concentration sensor because of a corresponding activation by the control unit. Finally, after the recording of the comparison measured value, a deviation of the comparison measured value from the reference value in relation to the predefined or predefinable expected value is checked by means of the control unit within the framework of the comparison. At the end of the method, a warning message is issued by means of the control unit or at least under the control thereof when the deviation does not or does not at least essentially correspond to the expected value.

The advantage of a test method based on a determination of at least one gas concentration measured value is that, in addition to a possible detection of transposed ventilation tubes, additional errors in the gas supply of the medical device in question may possibly also be detected, for example, when no oxygen is available via a connected oxygen supply line or when a connected gas cylinder is not filled or is not filled sufficiently with oxygen or when an incorrect internal tubing of the gas mixer of the medical device is present.

The advantage of the method, in which pressure measured values are determined, is that the reference state can be easily and reliably created in relation to a pressure measured value by ventilating (opening the breathing circuit). Pressure measured values can be recorded by means of a corresponding and comparatively cost-effective sensor mechanism and indeed be recorded both as reference values and as comparison measured values during the predefined operating state of the gas delivery unit. The resulting measured values (reference values and comparison values) are thus a good basis for a comparatively simple implementation of the test method according to the invention.

In a combination of the two variants, i.e., in case of a consideration of pressure measured values and gas concentration values, a redundant and diverse test method is obtained, which is hence particularly reliable because a carrying out of the test method and a detection of ventilation tubes connected in a transposed manner are still possible even in case of failure of a sensor mechanism, for example, of the sensor for recording the pressure measured values.

In an embodiment of the method, the comparison measured value (built up pressure the comparison measured value) is recorded at an end of a flank of a pressure curve (from measured values) in the breathing circuit, which flank is rising because of the buildup of pressure. A defined time for the recording of the comparison measured value is obtained from the end of the rising flank. An expected value can be especially readily indicated in regard to such a comparison measured value. This also correspondingly applies to the variant of the method based on a recording of gas concentration values.

After the buildup of pressure in the breathing circuit and the recording of the comparison measured value, a drop in pressure in the breathing circuit is automatically caused because of a corresponding activation by means of the control unit. A further comparison measured value (a dropped pressure comparison measured value) is recorded in the breathing circuit at the time of the drop in pressure, especially at the end of a resulting falling flank of the pressure curve. After the recording of the further comparison measured value, a deviation of the further comparison measured value from the reference value in relation to a further expected value is checked. After the test method complemented to this extent, a warning message is issued when the deviation does not or does not at least essentially correspond to the further expected value.

This method is therefore especially advantageous because an especially robust test method results because of taking two comparison measured values, namely the comparison measured value—first comparison measured value—and the further comparison measured value into consideration. The first comparison measured value recorded in chronological correlation with the buildup of pressure in the breathing circuit could also be generated by the Y-piece being short-circuited by means of a ventilation tube and being compressed during the buildup of pressure, for example, by stepping on the ventilation tube. The rise in pressure resulting therefrom and reaching the pressure sensor by means of the sample gas line does not result from the buildup of pressure in the breathing circuit because the short-circuited Y-piece is not connected to the breathing circuit at all. Even though an incorrect connection of the ventilation tubes is present, the analysis of the rise in pressure, which is detectable by means of the pressure sensor, could consequently lead to an incorrect analysis, which signals a correct connection in spite of the actually incorrect connection of the ventilation tubes, in case of such a special state, in which a user steps on the ventilation tube, short-circuiting the Y-piece. The consideration of two comparison measured values considerably reduces the at least theoretical risk of an incorrect analysis. By a comparison measured value, the further comparison measured value, being recorded at the time of the drop in pressure, especially at the end of a resulting falling flank, and being checked in relation to a corresponding expected value, an incorrect analysis in case of a short-circuited Y-piece could still be obtained only if, on the one hand, the ventilation tube short-circuiting the Y-piece is stepped on in suitable chronological correlation with the buildup of pressure occurring within the framework of the test method and, on the other hand, the foot is again removed from the ventilation tube in just as suitable chronological correlation with the drop in pressure occurring within the framework of the test method. It is extremely unlikely that a stepping on the ventilation tube and a removal of the foot from the ventilation tube produce the buildup of pressure and the drop in pressure in precisely the chronological correlation as according to the test method and subsequent thereto in each case the comparison measured values are recorded, so that a very reliable test method results.

In a test method taking into account a drop in pressure after a previously generated rise in pressure, provisions are made for the drop in pressure in the breathing circuit to be triggered by means of an activation of the venting device. An opening of the breathing circuit to the surrounding area brought about by an activation of the venting device brings about an especially significant and thus especially easily analyzable drop in pressure. As an alternative, the drop in pressure could also be generated by means of the gas delivery unit, for example, in the case of a gas delivery unit with an impeller by reversing the direction of rotation or in case of a gas delivery unit in the form of a piston cylinder unit by a vacuum being generated in the breathing circuit by means of a corresponding piston motion.

Even though the test method was described above on the basis of a buildup of pressure occurring in the breathing circuit as well as—in a special embodiment—on the basis of a buildup of pressure and a subsequent drop in pressure, the gas delivery unit in special medical devices may also generate a vacuum in the breathing circuit at least during a test state. The analysis of the comparison measured value and of the further comparison measured value may therefore be carried out in exactly the same way on the basis of an inverse sequence of the resulting pressure curve edge—curve flanks—and a corresponding variant shall always be considered to be covered by the description presented here and can also be read correspondingly in each case.

Exemplary embodiments of the present invention are explained in detail below on the basis of the drawing. Subjects or components corresponding to one another are provided with identical reference numbers in all figures. Variants and modifications are possible within the framework of the present disclosure, and in particular such variants and combinations, which, for example, can be derived for the person skilled in the art in regard to accomplishing the object by combining or modifying individual features in conjunction with the features described in the general or special section of the specification as well as contained in the claims and/or drawings, and lead to a new subject by combinable features. The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
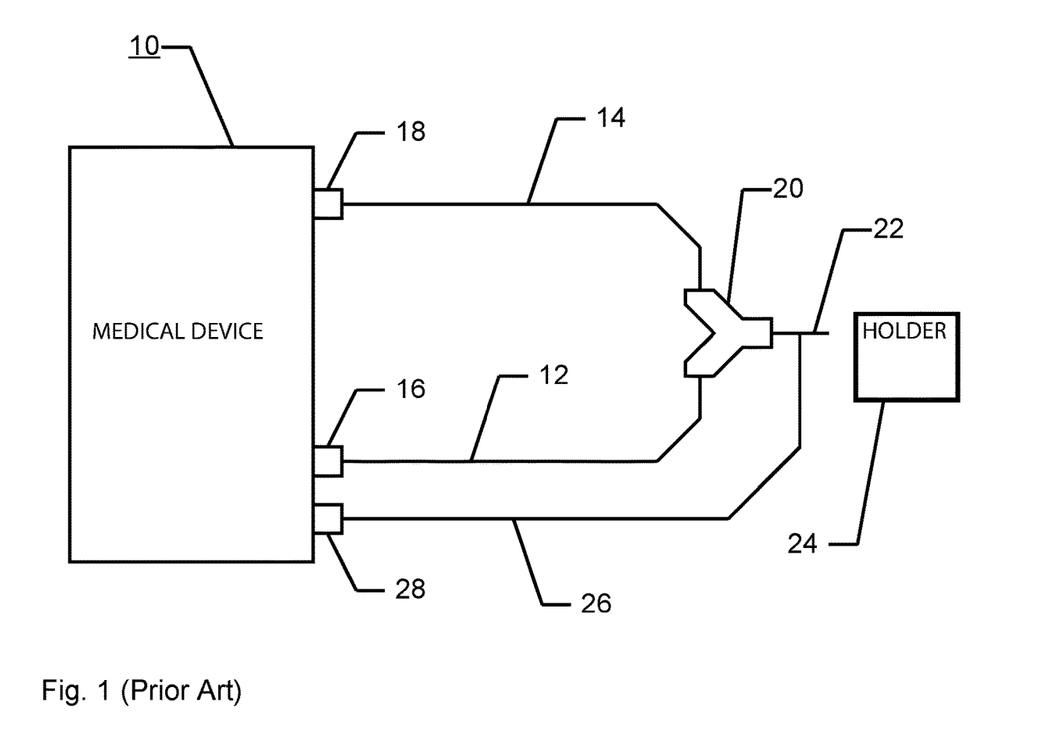
FIG. 1 is a schematic view showing a medical device with ventilation tubes.

Referring to the drawings, FIG. 1 shows in a schematically highly simplified manner a ventilator or anesthesia device, which is designated here and below in summary as medical device 10 or sometimes also only briefly as device 10, with ventilation tubes 12, 14 connected to it. The medical device 10 comprises in a manner known per se an inspiratory fluidic port 16 and an expiratory fluidic port 18 (sometimes briefly designated below as inspiratory port 16 and expiratory port 18). The ventilation tubes 12, 14 connected thereto in each case are correspondingly also designated as inspiratory ventilation tube 12 and expiratory ventilation tube 14 or briefly as inspiratory tube 12 and expiratory tube 14.

The two ventilation tubes 12, 14 are joined to a so-called Y-piece 20, i.e., are connected to the Y-piece 20, in a manner known per se. A tube 22 leads to the patient downstream of the Y-piece 20. The Y-piece 20 can be deposited in a parking holder 24, which is shown without further details.

Besides the ventilation tubes 12, 14, a sample gas line 26 for a gas measurement is connected to the Y-piece 20. The sample gas line 26 is guided to a fluid measuring port (sample gas port) 28 at the medical device 10.

Figure 2:
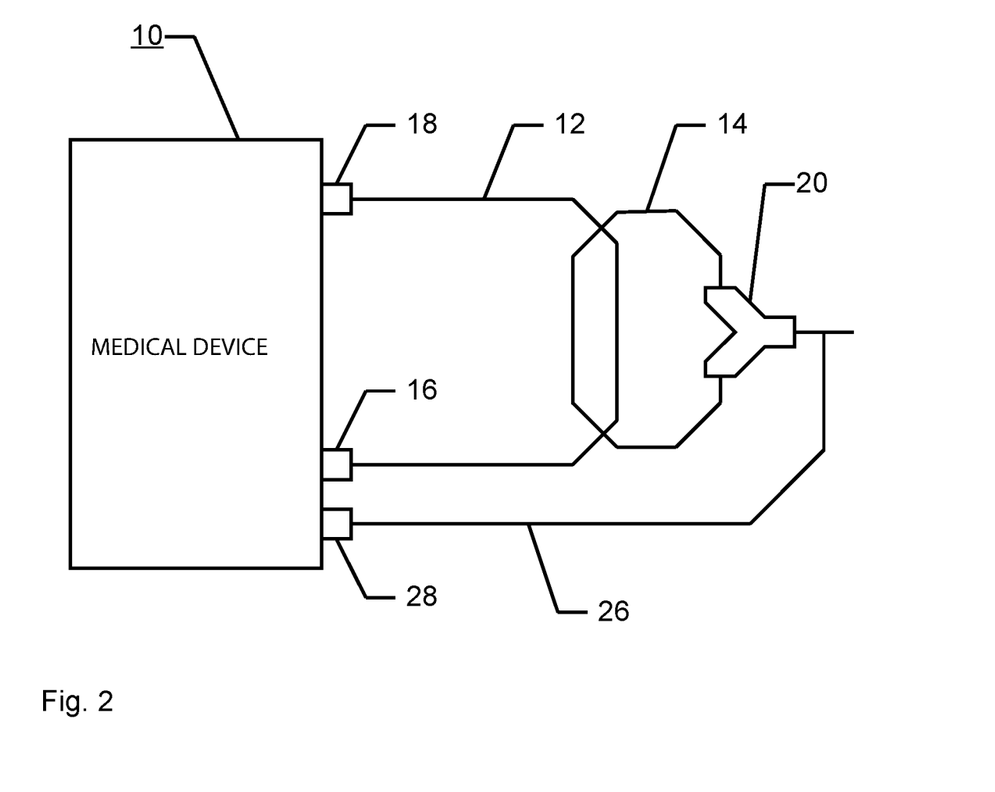
FIG. 2 is a schematic view showing a device as in FIG. 1 with incorrectly connected ventilation tubes.

The view in FIG. 2 shows in a likewise schematically simplified manner a medical device 10 as in FIG. 1, but with incorrectly connected ventilation tubes 12, 14, namely ventilation tubes connected in a transposed manner. The incorrect, transposed connection includes a first ventilation tube 12 being connected both to the inspiratory port 16 as well as to the expiratory port 18 (short-circuit) and by the two connections of the Y-piece 20 facing away from the tube leading to the patient being likewise short-circuited by means of a further ventilation tube 14. Such a transposed connection of the ventilation tubes 12, 14 represents a special (incorrect) fluidic connection state of the device 10 and may absolutely occur in practice because of a plurality of tubes, i.e., further tubes, not shown here, and/or cables in the nursing care area or patient area, besides the ventilation tubes 12, 14.

Figure 3:
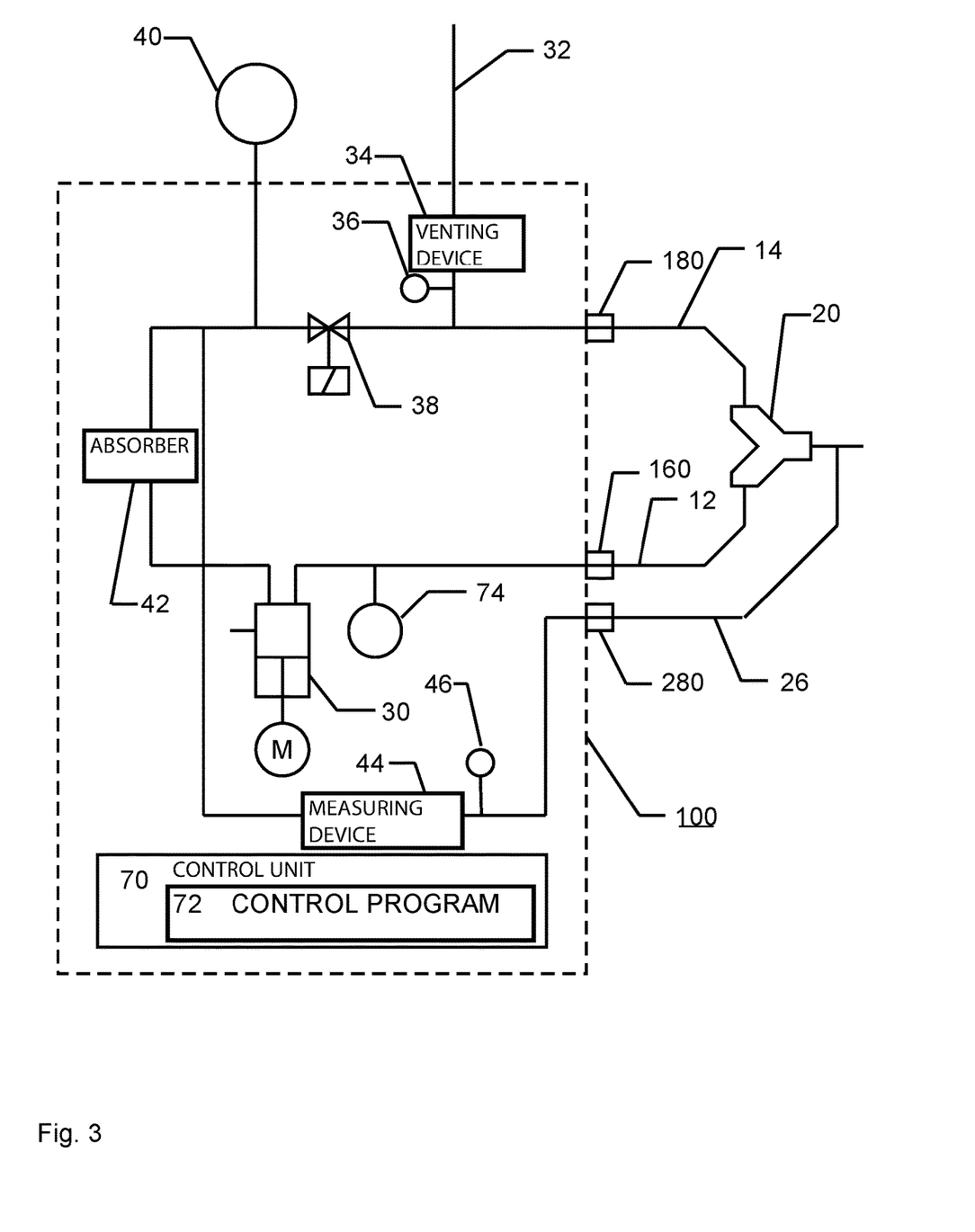
FIG. 3 is a schematic view showing a medical device according to the invention with features for an automatic detection of transposed or incorrectly connected ventilation tubes.

The view in FIG. 3 shows a medical device 100 of the type mentioned in the introduction according to an embodiment of the invention, shown in a schematically simplified manner. The medical device 100 is configured to automatically detect a special fluidic connection state in the form of transposed ventilation tubes 12, 14.

The medical device 100 comprises a gas delivery unit 30, which is, in principle, known per se and is hence also shown without specific details and is functioning as a ventilation drive, for example, in the form of a piston cylinder unit. Viewed counterclockwise, the gas delivery unit 30 is connected to the so-called inspiratory branch and, via an inspiratory port 160, with the inspiratory ventilation tube 12 connected to the Y-piece 20. The expiratory ventilation tube 14 is, moreover, connected to the Y-piece 20 and connects via expiratory port 180, with the expiratory branch within the device 100. A vent line 32 is connected to the expiratory branch. By means of the vent line 32, the expiratory branch can be coupled to ambient air and ambient pressure for venting, and the vent line 32 is usually closed. A safety valve functioning as a venting device 34 is shown in the embodiment shown in FIG. 3 for closing the vent line 32. A pressure sensor 36 is provided on the side of the venting device 34 facing the expiratory branch. The pressure conditions in the expiratory branch can be detected by means of the pressure sensor 36. Proceeding counterclockwise, located after the vent line 32 in the expiratory branch is a so-called PEEP valve 38, which guarantees a maintenance of the so-called positive end-expiratory pressure (PEEP), especially in an embodiment as a proportional valve. Proceeding further counterclockwise, a ventilation bag 40, which is, in principle, optional, is shown after the PEEP valve 38 as an aid for the manual ventilation of a patient. The PEEP valve 38 may also function as a venting device together with a further valve (not shown), arranged, for example, in the vicinity of the ventilation bag 40. In general, any other creation of a reference pressure state shall also be included by the term venting and, in this respect, any device intended for creating a reference pressure state, even if such device creates the reference pressure state, for example, not by a venting to the surrounding area, is considered to be a venting device. The circuit (breathing circuit) shown is connected by means of a connection to the gas delivery unit 30 via an optional absorber 42, which is provided for removing the carbon dioxide ($CO_2$) from the exhaled gas flowing through the expiratory branch. In the shown closed form of the breathing circuit, gas may also be suctioned by means of the gas delivery unit 30, for example, from the ventilation bag 40 and be delivered into the inspiratory branch.

In the embodiment shown, the sample gas line 26 is indirectly coupled to the expiratory branch and indeed via a gas measured device 44 for the sample gas measurement, which is usually designated as a patient gas analyzer (PGA). A pressure sensor 46 is placed upstream of the gas measuring device 44 for determining the pressure conditions in the sample gas line 26.

The method for the automatic detection of a possible transposition of the ventilation tubes 12, 14 is based, in one embodiment, on a pressure measurement in the sample gas line 26 by means of the pressure sensor 46. The Y-piece 20 is closed with a plug or the like upstream of the connection of the sample gas line 26 during the course of the method and is located, for example, in a parking holder 24. The method (test method) is schematically shown in a simplified manner in the view in FIG. 4 in the form of a flow chart 50 for illustrating the individual method steps 52-58 comprised by the method. A graph 60 is additionally shown in the view in FIG. 5 on conditions developing during the individual test steps 52-58 within the framework of the test method.

Figure 4:
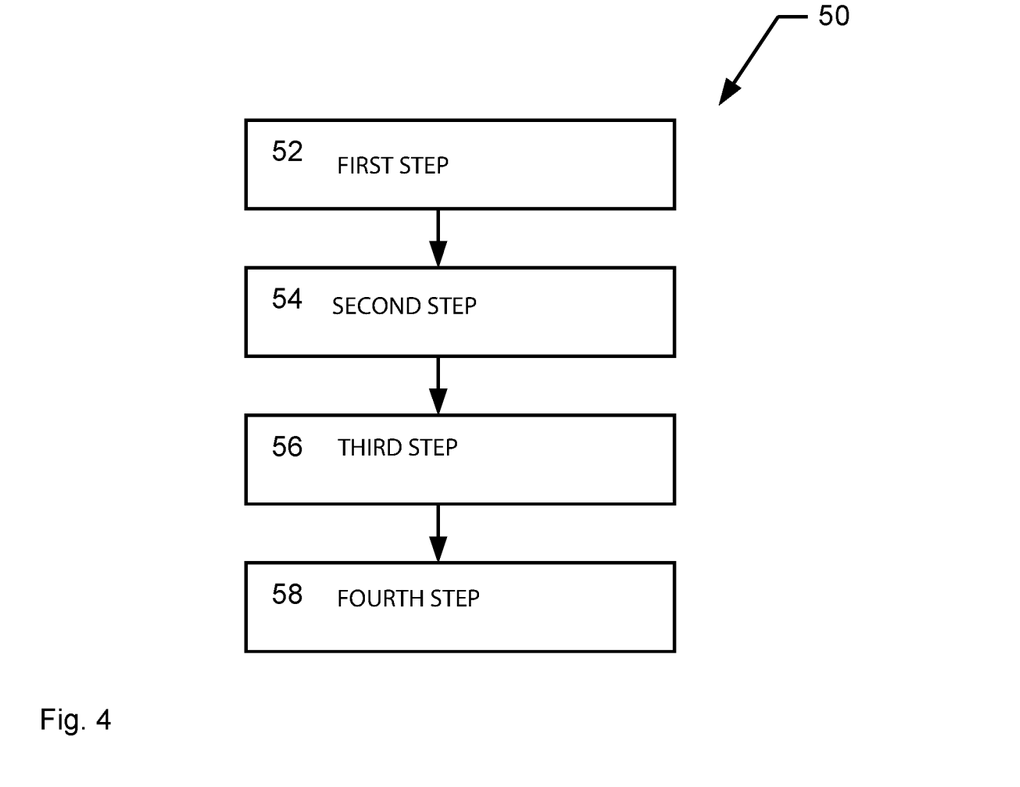
FIG. 4 is a flow chart on a test method carried out in the automatic detection of ventilation tubes connected in a transposed manner.

First, pressure is released from the entire breathing circuit by means of the venting device 34 in a first step 52 of the test method. For this, the venting device 34, here consequently the safety valve, is activated, for a predefined or predefinable period of time such that the venting device 34 is opened to the surrounding area. At the same time or in conjunction therewith, a suctioning of sample gas through the sample gas line 26 is stopped by means of the gas measuring device 44. The venting can be monitored and checked by means of the pressure sensor 36 associated with the vent line 32.

Figure 5:
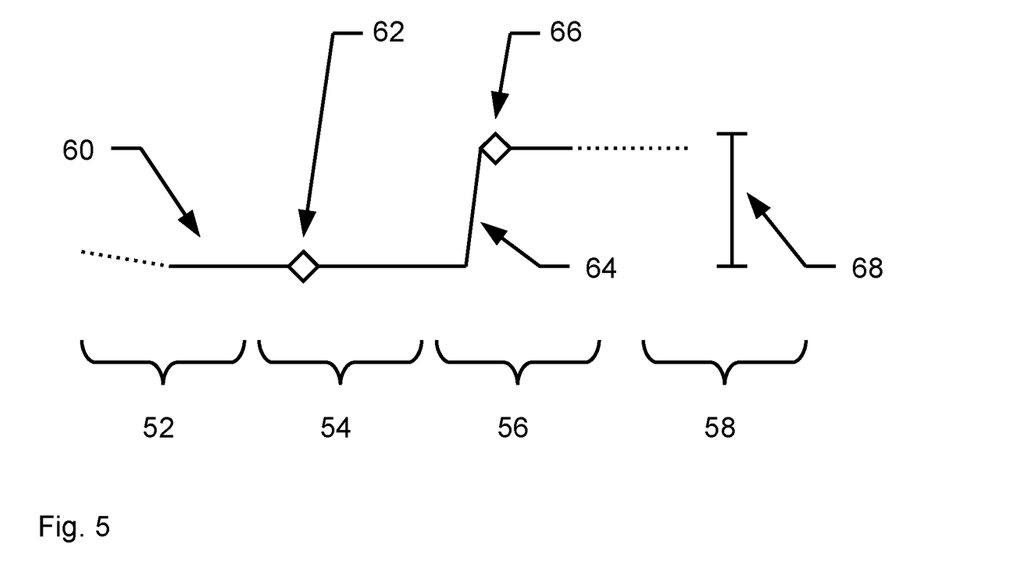
FIG. 5 is a graph showing pressure conditions resulting within the framework of the test method.

The graph 60 shown in FIG. 5 is a graph of the pressure conditions detected by means of the pressure sensor 46. The pressure sensor 46 is located after the sample gas line 26 connected to the Y-piece 20. An incorrect connection of the sample gas line 26 to the Y-piece 20 does not usually have to be expected because the sample gas line 26 has a different, especially smaller, cross section in comparison to the ventilation tubes 12, 14 such that the sample gas line 26 can be connected to the Y-piece 20 only as intended. A pressure approaching ambient pressure gradually develops in the breathing circuit during the venting. This is shown, for example, in the form of a falling curve of the graph 60 in the view in FIG. 5.

In a second step 54 of the test method, a current pressure measured value is recorded by the pressure sensor 46 as a reference value 62. In the view in FIG. 5, the reference value 62 is shown as a dot of the graph 60 in a period of time belonging to the second test step 54. The venting device 34 is closed after the recording of the reference value 62.

The gas delivery unit 30, i.e., for example, the piston cylinder unit shown, is started for obtaining a predefined operating state of the gas delivery unit 30 in a third step 56 of the test method. A positive pressure curve edge (flank) 64 of, for example, 20 hPa occurs because of the resulting buildup of pressure in the breathing circuit. The curve edge (flank) 64 and a resulting pressure measured value at the end of the curve edge (flank) 64 can be determined by means of the pressure sensor 46. The pressure measured value at the end of the curve edge (flank) 64 is determined and temporarily stored as a comparison measured value 66. At the end of the third test step 56 of the test method, the comparison measured value 66 is compared with the previously recorded reference value 62. If the change in the pressure conditions detected by means of the pressure sensor 46, in this case the rise in pressure, i.e., the difference from the comparison measured value 66 and the reference value 62, corresponds to a predefined or predefinable expected value 68 according to the rise in pressure applied by the gas delivery unit 30 minus a predefined or predefinable tolerance, it can be ruled out that the ventilation tubes 12, 14 are transposed during the connection to the Y-piece 20. On the other hand, if the detected change in the pressure conditions do not correspond to the expected value 68 minus tolerance, a warning message is issued, for example, by activating an optical and/or acoustic signal or display element, not shown, in a fourth test step 58 of the test method. A corresponding display may optionally also be triggered in the fourth test step 58, when it was determined with certainty by means of the test method that no transposition state is present.

Figure 6:
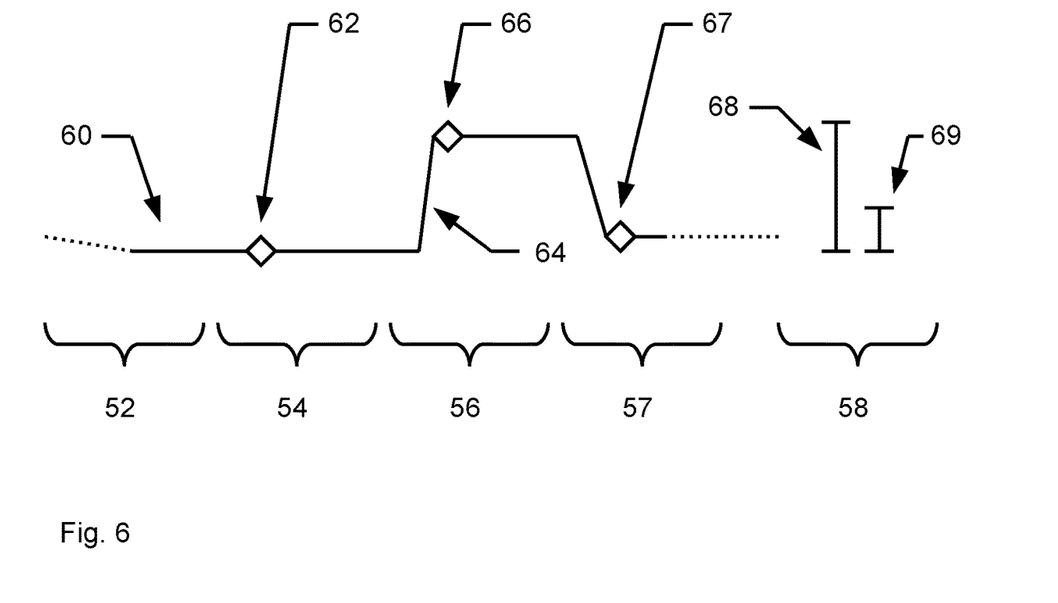
FIG. 6 is a graph showing pressure conditions resulting in a special embodiment of the test method.

The view in FIG. 6 shows a resulting graph 60 of the pressure conditions in a special embodiment of the test method. During the first, second and third test steps 52, 54, 56, the course of this special embodiment of the test method corresponds to the course already described. After the third test step 56 (starting the gas delivery unit to obtain a predefined operating state) and the buildup of pressure in the breathing circuit brought about thereby, a drop in pressure in the breathing circuit is generated in an additional test step 57. The drop in pressure may be obtained, for example, by the venting device 34 being automatically correspondingly activated. Because of the drop in pressure, a falling curve edge (curve flank) results, and a further comparison measured value 67 is recorded as a pressure measured value in conjunction with the drop in pressure, especially at the end of the falling flank or after passing a predefined or predefinable period of time after triggering the drop in pressure. The further comparison measured value 67 can be analyzed analogously to the analysis of the comparison measured value 66. After the recording of the further comparison measured value 67, a deviation of the further comparison measured value 67 from the reference value 62 in relation to a further expected value 69 is then checked. A warning message is issued when the deviation does not or does not at least essentially correspond to the further expected value 69.

The course of the test method is automatically controlled and monitored by means of a control unit 70 (FIG. 3) comprised by the medical device 100. The test method is automatically triggered every time the device 100 is switched on and/or before a patient is connected by the user. The control unit 70 comprises, for example, in a manner known per se, a processing unit in the form or manner of a microprocessor as well as a memory, in which a control program 72 with an implementation of the test method is loaded, so as to configure the control unit. The control unit 70 is connected to the functional units of the device 100, i.e., at least the gas delivery unit 30, the venting device 34 and the pressure sensor 46, which are used within the framework of the test method, for carrying out the test method. For the sake of clarity of the view in FIG. 3, corresponding line connections are not shown. During the carrying out of the individual method steps 52-58 of the test method and/or during the transition from one method step 52-58 to a next method step 52-58, the control unit 70 monitors, on the basis of the control program 72, predefined or predefinable periods of time, for example, a period of time after activating the venting device 34, during which the breathing circuit is vented or a sufficient venting of the breathing circuit can be expected after the passing of this period of time. The monitoring of predefined conditions may also be carried out instead of monitoring such periods of time. Sufficient venting can be detected during the venting of the breathing circuit, for example, on the basis of a measured value of the pressure sensor 36. In exactly the same manner, a measured value can be recorded at the end of a rising flank 64 or at the end of a falling flank of a measured value curve by the course of a predefined or predefinable period of time after an action triggering the rising flank 64 or the falling flank being expected for this by means of the control unit 70. As an alternative, the measured value curve itself may also be monitored by means of the control unit 70 such that the recording of the corresponding measured value is not carried out in a time-dependent manner, but rather because of the detected end of the corresponding curve edge—curve flank.

The described method may also be carried out on the basis of flow measured values instead of taking into account pressure measured values and a resulting reference value 62 and comparison measured value 66 as well as possibly a further comparison measured value 67. Corresponding flow measured values then take the place of the hitherto mentioned pressure measured values. Many measuring devices 44 functioning as PGA already comprise a sensor for determining flow measured values and the measuring device 44 is correspondingly conceived here itself as a flow sensor. A regulation, which has the goal of a constant flow through the measuring device 44, is possible by means of such a sensor. Like the pressure sensor 46, the sensor in question can be used for determining the corresponding measured values within the framework of the test method. When—as described above—a suctioning of sample gas through the sample gas line 26 is stopped by means of the measuring device 44 in conjunction with the carrying out of the test method, a flow detectable by means of the flow sensor is the result of an activation of the gas delivery unit 30 possibly carried out within the framework of the test method. The flow measured values that can be obtained may thus be used for the detection of transposed ventilation tubes 12, 14, just as this was described previously on the basis of the pressure measured values. When the pressure of the gas delivery unit 30 consequently generates a pressure at the Y-piece 20 and the sample gas line 26 is connected to the measuring device 44 and to the flow sensor, a flow is generated through the measuring device 44 and the flow sensor. If, on the other hand, a flow cannot be measured, this is an indication that the sample gas line 26 is not connected or the error of a transposition of the ventilation tubes 12, 14 to be detected is present.

The determination and analysis of flow measured values can be carried out parallel with and/or complementary to the determination and analysis of pressure measured values. In case of a resulting combined test method, a redundant and diverse test method, which is especial reliable, is obtained because it is still possible to carry out the test method and to detect the incorrect connection of a ventilation tube 12, 14 even in case of failure of a sensor mechanism, for example, of the pressure sensor 46 for recording the pressure measured values.

The test may also be carried out on the basis of gas concentration measured values by means of an optional and hitherto not considered gas mixer 74—likewise under the control of the control unit 70. For this—if the creation of a reference state is provided at the beginning of the test method—the breathing circuit is first flushed with a gas with a known gas concentration (for example, about 21% oxygen in ambient air) by means of the gas mixer 74 or via the ambient air and within the framework of a first method step 52. A pump comprised by the gas measuring device 44 is started for recording the reference value 62 such that the sample gas used for flushing the breathing circuit is suctioned into the sample gas line 26 and to the sensor 46 functioning here as a gas concentration sensor. A gas concentration measured value can then be determined as a reference value 62 by means of the sensor 46 in a second method step 54. Subsequently, a test gas or a defined quantity of test gas (for example, 100% oxygen) is metered into the breathing circuit by means of the gas mixer 74 during a defined time in a third method step 56. A gas concentration measured value is recorded as a comparison measured value 66 by means of the sensor 46 at the end of a resulting rising flank 64 in the concentration curve of the gas in question, for example, oxygen, or after passing a predefined or predefinable period of time. The analysis of the resulting comparison measured value 66 or of the comparison measured value 66 and of the reference value 62 is carried out analogously to the analysis already described and based on pressure measured values. Just as this is shown in the view in FIG. 6, a falling curve edge—curve flank—in the gas concentration in question in each case can be generated after the metering of a sample gas, for example, by the breathing circuit being opened by means of the venting device 34 and consequently ambient air finding its way into the breathing circuit instead of the sample gas. Unlike the analysis based on pressure measured values, provisions are made in an analysis based on gas concentration measured values for the pump comprised by the measuring device 44 or another delivery unit acting for delivering gas through the sample gas line 26 to the sensor 46 running during the test method, at least, however, before and during the recording of the reference value 62 as well as before and during the recording of the comparison measured value 66 and possibly also before and during the recording of the further comparison measured value 67, and a corresponding delivery of gas from the breathing circuit to the sensor 46 being brought about.

Finally, individual essential aspects of the description presented here can be briefly summarized as follows: A method and a corresponding device are provided for detecting incorrectly connected or transposed ventilation tubes 12, 14 of a medical device 100, in which method or in which device a measured value is determined as a comparison measured value 66 by means of a sensor 46 chronologically correlated with a predefined operating state of a gas delivery unit 30 of the device 100 and this value is compared with a predefined or predefinable expected value 68, and a warning message is possibly issued depending on the result of the comparison.

While specific embodiments of the invention have been shown and described in detail to illustrate the application of the principles of the invention, it will be understood that the invention may be embodied otherwise without departing from such principles.

What is claimed is:

1. A method for automatic detection of a fluidic connection state of a ventilator or anesthesia device, wherein the ventilator or anesthesia device comprises a gas delivery unit, at least one pressure sensor or flow sensor, a control unit, an inspiratory fluidic port, an expiratory fluidic port and a fluid measuring port, which is coupled with the at least one pressure sensor or flow sensor, wherein the inspiratory fluidic port and the expiratory fluidic port is configured to be coupled to a Y-piece, as part of a breathing circuit, via ventilation tubes and wherein the fluid measuring port is configured to be coupled to the Y-piece by means of a sample gas line, the method comprising steps carried out under a control of the control unit comprising:
creating a reference state;
recording a measured value as a reference value during the reference state;
ending the reference state after the recording of the reference value;
activating the gas delivery unit after the ending of the reference state;
creating a buildup of pressure in the breathing circuit with the gas delivery unit;
determining a comparison measured value with the at least one pressure sensor or flow sensor in the form of a pressure measured value or flow value relating to the buildup of pressure;
comparing the built up pressure comparison measured value with a predefined or predefinable expected value, wherein a built up pressure deviation of the built up pressure comparison measured value from the reference value relative to the predefined or predefinable expected value is monitored based on the comparison;
issuing a warning message based on the built up pressure deviation and the expected value;
causing a drop in pressure in the breathing circuit after the ending of the reference state;
recording a dropped pressure comparison measured value relating to the drop in pressure;
comparing the dropped pressure comparison measured value with a predefined or predefinable further expected value, wherein a dropped pressure deviation of the dropped pressure comparison measured value from the reference value relative to the predefined or predefinable further expected value is monitored based on the comparison; and
issuing a further warning message based on the dropped pressure deviation and the further expected value.

2. A method in accordance with claim 1, wherein:
the ventilator or anesthesia device comprises at least one venting device;
the reference state is created by the breathing circuit being opened by the at least one venting device;
the reference value is a pressure measured value or a flow measured value recorded by means of the at least one pressure sensor or flow sensor; and the method further comprising:
ending the reference state after the recording of the reference value including closing the breathing circuit by closing the at least one venting device.

3. A method in accordance with claim 2, wherein the built up pressure comparison measured value is recorded at an end of a rising flank, which is a result of the buildup of pressure, of a pressure curve of the pressure within the breathing circuit.

4. A method in accordance with claim 2, wherein the drop in pressure in the breathing circuit is triggered by means of an activation of the at least one venting device.

5. A method in accordance with claim 1, wherein:
determining a built up pressure comparison measured value with the pressure sensor or flow sensor in the form of a pressure measured value or flow value relating to the buildup of pressure; and
comparing the built up pressure comparison measured value with a predefined or predefinable expected value, wherein a deviation of the built up pressure comparison measured value from the reference value in relation to the predefined or predefinable expected value is monitored based on the comparison occur prior to:

recording a dropped pressure comparison measured value relating to the drop in pressure; and
comparing the dropped pressure comparison measured value with a predefined or predefinable further expected value, wherein a deviation of the dropped pressure comparison measured value from the reference value in relation to the predefined or predefinable further expected value is monitored based on the comparison.

6. A method in accordance with claim 1, wherein:
recording a dropped pressure comparison measured value relating to the drop in pressure; and
comparing the dropped pressure comparison measured value with a predefined or predefinable further expected value, wherein a deviation of the dropped pressure comparison measured value from the reference value in relation to the predefined or predefinable further expected value is monitored based on the comparison occur prior to:
determining a built up pressure comparison measured value with the pressure sensor or flow sensor in the form of a pressure measured value or flow value relating to the buildup of pressure; and
comparing the built up pressure comparison measured value with a predefined or predefinable expected value, wherein a deviation of the built up pressure comparison measured value from the reference value in relation to the predefined or predefinable expected value is monitored based on the comparison.

7. A ventilator or anesthesia device comprising:
a gas delivery unit;
at least one pressure sensor or flow sensor;
an inspiratory fluidic port;
an expiratory fluidic port;
a fluid measuring port coupled with the at least one pressure sensor or flow sensor, wherein the inspiratory fluidic port and the expiratory fluidic port are coupleable to a Y-piece via ventilation tubes to provide a breathing circuit and wherein the fluid measuring port is coupleable to the Y-piece via a sample gas line;
a control unit configured to:
create a reference state;
record a measured value as a reference value during the reference state;
end the reference state after the recording of the reference value;
activate the gas delivery unit after the ending of the reference state including create a buildup of pressure in the breathing circuit with the gas delivery unit;
determine a built up pressure comparison measured value with the at least one pressure sensor or flow sensor in the form of a pressure measured value or flow value relating to the buildup of pressure;
compare the built up pressure comparison measured value with a predefined or predefinable expected value, wherein a built up pressure deviation of the built up pressure comparison measured value from the reference value relative to the predefined or predefinable expected value is monitored based on the comparison;
issue a warning message based on the built up pressure deviation and the expected value;
cause a drop in pressure in the breathing circuit after the ending of the reference state;
record a dropped pressure comparison measured value relating to the drop in pressure;
compare the dropped pressure comparison measured value with a predefined or predefinable further expected value, wherein a dropped pressure deviation of the dropped pressure comparison measured value from the reference value relative to the predefined or predefinable further expected value is monitored based on the comparison; and
issue a further warning message based on the dropped pressure deviation and the further expected value.

8. A ventilator or anesthesia device according to claim 7, further comprising at least one venting device, wherein:
the reference state is created by the breathing circuit being opened by the at least one venting device; and
the control unit ends the reference state after the recording of the reference value including closing the at least one venting device to close the breathing circuit.

9. A ventilator or anesthesia device according to claim 8, wherein the comparison measured value is recorded at an end of a rising flank, which is a result of the buildup of pressure, of a pressure curve of the pressure in the breathing circuit.

10. A ventilator or anesthesia device according to claim 8, wherein the drop in pressure in the breathing circuit is triggered by means of an activation of the at least one venting device.

11. A ventilator or anesthesia device according to claim 8, wherein control unit is configured to:
determine a built up pressure comparison measured value with the pressure sensor or flow sensor in the form of a pressure measured value or flow value relating to the buildup of pressure; and
compare the built up pressure comparison measured value with a predefined or predefinable expected value, wherein a deviation of the built up pressure comparison measured value from the reference value in relation to the predefined or predefinable expected value is monitored based on the comparison prior to:
recording a dropped pressure comparison measured value relating to the drop in pressure; and
comparing the dropped pressure comparison measured value with a predefined or predefinable further expected value, wherein a deviation of the dropped pressure comparison measured value from the reference value in relation to the predefined or predefinable further expected value is monitored based on the comparison.

12. A ventilator or anesthesia device according to claim 8, wherein control unit is configured to:
record a dropped pressure comparison measured value relating to the drop in pressure; and
compare the dropped pressure comparison measured value with a predefined or predefinable further expected value, wherein a deviation of the dropped pressure comparison measured value from the reference value in relation to the predefined or predefinable further expected value is monitored based on the comparison prior to:
determining a built up pressure comparison measured value with the pressure sensor or flow sensor in the form of a pressure measured value or flow value relating to the buildup of pressure; and
comparing the built up pressure comparison measured value with a predefined or predefinable expected value, wherein a deviation of the built up pressure comparison measured value from the reference value in relation to the predefined or predefinable expected value is monitored based on the comparison.

13. A method for automatic detection of a fluidic connection state, the method comprising the steps of:

providing a ventilator or anesthesia device comprising a gas delivery unit, at least one pressure sensor or flow sensor, a control unit, an inspiratory fluidic port, an expiratory fluidic port and a fluid measuring port, which is coupled with the at least one pressure sensor or flow sensor, wherein the inspiratory fluidic port and the expiratory fluidic port are connectable with ventilation tubes which are connectable with a Y-piece, to form a breathing circuit with the ventilator or anesthesia device and the fluid measuring port can be coupled to the Y-piece by a sample gas line;

with the control unit initiating a reference state;

with the control unit recording a measured value as a reference value during the reference state;

with the control unit ending the reference state after the recording of the reference value;

with the control unit activating the gas delivery unit, after the ending of the reference state, including creating a buildup of pressure in the breathing circuit with the gas delivery unit;

with the control unit determining a comparison measured value with the at least one pressure sensor or flow sensor in the form of a pressure measured value or flow measured value after ending the reference state and after the build up of pressure in the breathing circuit;

with the control unit determining a difference between the comparison measured value and the reference value;

with the control unit comparing the difference with a predefined or predefinable expected value, wherein a deviation of the comparison measured value from the reference value relative to the predefined or predefinable expected value is monitored based on the comparison;

with the control unit issuing a warning message depending on a result of the comparison;

with the control unit causing a drop in pressure in the breathing circuit after the buildup of pressure in the breathing circuit and after the recording of the comparison measured value;

with the control unit recording a further comparison measured value following the drop in pressure;

with the control unit determining a further difference between the further comparison measured value and the reference value;

with the control unit comparing the further difference with a further predefined or predefinable expected value, wherein a deviation of the further comparison measured value from the reference value relative to a further expected value monitored based on the comparison; and with the control unit issuing a further warning message depending on a result of the comparison of the further difference.

14. A method according with claim 13, wherein:

the ventilator or anesthesia device further comprises at least one venting device;

the reference state is created by the breathing circuit being opened by the at least one venting device; and the control unit ends the reference state after the recording of the reference value including closing the at least one venting device to close the breathing circuit.

15. A method according to claim 14, wherein the drop in pressure in the breathing circuit is triggered by means of an activation of the venting device.

16. A method according to claim 14, wherein the comparison measured value is recorded at an end of a rising flank, which is a result of the buildup of pressure, of a pressure curve of pressure in the breathing circuit.

17. A method according to claim 13, wherein the predefined or predefinable expected value includes a tolerance.

* * * * *